United States Patent
Baum et al.

[11] Patent Number: 6,111,124
[45] Date of Patent: Aug. 29, 2000

[54] LEWIS BASE ADDUCTS OF ANHYDROUS MONONUCLEAR TRIS(β-DIKETONATE) BISMUTH COMPOSITIONS FOR DEPOSITION OF BISMUTH-CONTAINING FILMS, AND METHOD OF MAKING THE SAME

[75] Inventors: Thomas H. Baum, New Fairfield, Conn.; Raymond H. Dubois, Mesa, Ariz.

[73] Assignee: Advanced Technology Materials, Inc., Danbury, Conn.

[21] Appl. No.: 09/224,614

[22] Filed: Dec. 31, 1998

Related U.S. Application Data

[63] Continuation-in-part of application No. 08/960,915, Oct. 30, 1997, Pat. No. 5,859,274.

[51] Int. Cl.$^7$ ............................................. C07F 9/94
[52] U.S. Cl. .................................. 556/76; 556/64
[58] Field of Search ............................ 556/76, 64

[56] References Cited

PUBLICATIONS

K.C. Brooks, et al. "Synthesis and Characterization of Volatile Bismuth Beta–Diketonate Compounds for Metal–Organic Chemical Vapor Deposition of Thin Films" Chem. Mater., vol. 4, 1992, pp. 912–916.

A.P. Pisarevskii et al., "Bismuth(III) Beta–Diketonates", Russ. J. of Inorg. Chem., 37(1), 1992, pp. 38–40.

G.K. Fukin, "Crystal and Molecular Strcture of Bismuth Dipavaloylmethanate", Russ. J. of Inorg. Chem., 38(7), 1993, pp. 1118–1123.

CA:129:324600 by Roeder in Integr. Ferroelectr., 21(1–4), pp. 367–379, 1998.

CA:129:103343 by Armelao in Inorg. Chim. Acta 275–276 (1,2), pp. 340–348, 1998.

CA:120:42314 by Fukin lin Zh. Neorg Khim 38(7) pp. 1205–1211, 1993.

CA:121:147729 by Zharkova in Koord Khim 20(2) pp. 101–105, 1994.

*Primary Examiner*—Gary Geist
*Assistant Examiner*—Jean F Vollano
*Attorney, Agent, or Firm*—Oliver A. Zitzmann

[57] ABSTRACT

Anhydrous mononuclear Lewis base adducted tris(β-diketonato) bismuth complexes, useful as precursors for chemical vapor deposition of bismuth, for producing Bi-containing films of significantly improved stoichiometry, morphology and functional character, as compared to films obtained from dinuclear tris(β-diketonato) bismuth complexes of the prior art.

24 Claims, 7 Drawing Sheets

LEWIS BASE ADDUCTS OF ANHYDROUS MONONUCLEAR TRIS(β-DIKETONATE) BISMUTH COMPOSITIONS FOR DEPOSITION OF BISMUTH-CONTAINING FILMS, AND METHOD OF MAKING THE SAME

This application is a continuation in part of Ser. No. 08/960,915 filed Oct. 30, 1997, now U.S. Pat. No. 5,859,274.

BACKGROUND OF THE INVENTION

1. Field of the Invention

This invention relates to the synthesis and production of Lewis base adducts of anhydrous mononuclear tris(β-diketonate) bismuth compositions e.g., anhydrous mononuclear tris-(2,2,6,6-tetramethyl-3,5-heptanedionato) bismuth N,N,N'N'-tetramethylethylenediamine adduct. Such bismuth-containing compositions have utility as precursors for chemical vapor deposition of bismuth, bismuth oxide, bismuth-containing oxides and bismuth-containing chalcogonides.

2. Description of the Related Art

Ferroelectric random access memories (FRAMs) rely on high-integrity ferroelectric thin-films as critical components of memory cell architecture.

Electrical performance of ferroelectric oxides such as $SrBi_2Ta_2O_9$ (SBT) show a strong dependence on the identity of the precursor used in depositing the Bi component in the ferroelectric material. For example, the use of a Bi precursor such as triphenyl bismuth results in poor stoichiometric control, high substrate temperatures to decompose the precursor, strong surface dependence, and extreme dependence of the precursor incorporation efficiency on reactor pressure and partial pressure of oxygen during deposition.

To ameliorate the foregoing deficiencies, the art has continued to seek other bismuth precursors.

One such bismuth-containing precursor candidate is tris (2,2,6,6-tetramethyl-3,5-heptanedionato) bismuth tetramethylethylenediamine adduct. As used hereinafter, the ligand "2,2,6,6-tetramethyl-3,5-heptanedionato" is sometimes referred to by the designation "thd" and the tetramethylethylenediamine adduct is sometimes referred to by the designation "tmeda."

It is an object of the present invention to provide an improved class of bismuth precursors for deposition of Bi for applications such as ferroelectric thin film devices, chalcogonides and thermoelectric films.

Other objects and advantages of the present invention will be more fully apparent from the ensuing disclosure and appended claims.

SUMMARY OF THE INVENTION

The present invention relates to Lewis base adducts of anhydrous mononuclear tris(β-diketonate) bismuth compositions, and to a method of synthesis thereof. Such adducts of anhydrous mononuclear bismuth precursors have been discovered as novel compositions having unexpectedly superior properties in relation to dinuclear (β-diketonate) bismuth compositions of the prior art, in respect of their volatilization and deposition characteristics, which render the adducts of anhydrous mononuclear bismuth precursors of the present invention particularly suitable as CVD precursors. The adducts of anhydrous mononuclear bismuth compositions of the present invention therefore constitute a substantial advance in the art over the dinuclear tris(β-diketonate) bismuth precursors heretofore available.

The β-diketonato ligand of the anhydrous mononuclear tris(β-diketonate) bismuth compositions of the present invention may be any suitable type, including the illustrative β-diketonato ligand species set out in Table I below:

TABLE I

| β-diketonato ligand | Abbreviation |
| --- | --- |
| 2,2,6,6-tetramethyl-3,5-heptanedionato | thd |
| 1,1,1-trifluoro-2,4-pentanedionato | tfac |
| 1,1,1,5,5,5-hexafluoro-2,4-pentanedionato | hfac |
| 6,6,7,7,8,8,8-heptafluoro-2,2-dimethyl-3,5-octanedionato | fod |
| 2,2,7-trimethyl-3,5-octanedionato | tod |
| 1,1,1,5,5,6,6,7,7,7-decafluoro-2,4-heptanedionato | dfhd |
| 1,1,1-trifluoro-6-methyl-2,4-heptanedionato | tfmhd |

The Lewis base adducts of the anhydrous mononuclear tris(β-diketonate) bismuth compositions of the present invention may be any suitable type, including at least one adduct ligand selected from the group consisting of: amines, ethers, glymes, aryls and aryl amines, more specifically, $NH_3$, primary amines, secondary amines, tertiary amines, polyamines, monoglymes, diglymes, triglymes, tetraglymes, polyethers, aliphatic ethers, cyclic ethers, and more specifically, pyridine, toluene, tetrahydrofuran, N,N,N',N'-tetramethylethylenediamine and N,N,N',N',N"-pentamethyldiethylenetriamine.

The Lewis base adducts of the anhydrous mononuclear tris(β-diketonato) bismuth compositions of the invention have utility as precursors for the vapor-phase deposition of bismuth, as for example in the formation of ferroelectric thin films of $SrBi_2Ta_2O_9$ (SBT), or in the formation of superconducting films containing Bi. In such applications, the use of the adducted anhydrous mononuclear Bi source material provides for better thermal transport and flash vaporization leading to Bi-containing films of significantly improved stoichiometry, morphology and ferroelectric/superconducting character. These same issues are important to chalcogonides, skutterudites and other Bi-containing materials.

The synthesis of Lewis base adducted anhydrous mononuclear tris(β-diketonato) bismuth complexes of the present invention may be prepared by reacting at least one molar equivalent of the Lewis base adduct compound with the mononuclear tris(β-diketonato) bismuth of the current art or the dinuclear tris(β-diketonato) bismuth of the prior art in an aprotic solvent medium, under anaerobic conditions followed by removal of the aprotic solvent medium. Purification of the isolated reaction product bismuth complex, e.g., by recrystallization, should also be carried out in an aprotic medium under anaerobic conditions.

In one aspect, the invention relates to an anhydrous mononuclear Lewis base adducted bismuth complex, comprising the formula:

wherein:

A comprises a β-diketonato ligand and X comprises a Lewis base adduct.

In another aspect the present invention relates to an anhydrous mononuclear Lewis base adducted bismuth complex, comprising the formula:

wherein:

A comprises a β-diketonato ligand having the formula:

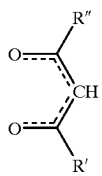

wherein:
R' and RΔ may be the same or different and are independently selected from H, $C_6$–$C_{10}$ aryl, $C_6$–$C_{10}$ fluoroaryl, $C_6$–$C_{10}$ perfluoroaryl, $C_1$–$C_6$ akyl, $C_1$–$C_6$ fluoroalkyl, and $C_1$–$C_6$ perfluoroalkyl; and X comprises at least one Lewis base adduct.

In another aspect the present invention relates to an anhydrous mononuclear Lewis base adducted bismuth complex, comprising the formula:

wherein:
A comprises a β-diketonato ligand selected from the group consisting of: thd, tfac, hfac, fod, tod, dfhd, tfmhd; and X comprises at least one Lewis base adduct selected from the group consisting of: amines, ethers, glymes, aryls and aryl amines, more specifically, $NH_3$, primary amines, secondary amines, tertiary amines, polyamines, monoglymes, diglymes, triglymes, tetraglymes, polyethers, aliphatic ethers, cyclic ethers, and more specifically, pyridine, toluene, tetrahydrofuran, N,N,N',N'-tetramethylethylenediamine and N,N,N',N',N"-pentamethyldiethylenetriamine.

In one specific method aspect, the present invention relates to a method of synthesis of N,N,N'N'-tetramethylethylenediamine adducted anhydrous mononuclear tris(2,2,6,6-tetramethyl-3,5-heptanedionato) bismuth, by reaction of dinuclear tris(2,2,6,6-tetramethyl-3,5-heptanedionato) bismuth complex and N,N,N'N'-tetramethylethylenediamine in an aprotic solvent under anaerobic conditions.

In another specific method aspect, the present invention relates to a method of synthesis of N,N,N',N','N"-pentamethyldiethylenetriainine adducted anhydrous mononuclear tris(2,2,6,6-tetramethyl-3,5-heptanedionato) bismuth, by reaction of dinuclear tris(2,2,6,6-tetramethyl-3, 5-heptanedionato) bismuth complex and N,N,N',N','N"-pentamethyldiethylenetriamine in an aprotic solvent under anaerobic conditions.

In another specific method aspect, the present invention relates to a method of synthesis of N,N,N',N','N"-pentamethyldiethylenetrianine adducted anhydrous mononuclear tris(2,2,6,6-tetramethyl-3,5-heptanedionato) bismuth, by reaction of anhydrous mononuclear tris(2,2,6, 6-tetramethyl-3,5-heptanedionato) bismuth and N,N,N',N', 'N"-pentamethyldiethylenetriamine in an aprotic solvent under anaerobic conditions.

The N,N,N'N'-tetramethylethylenediamine adducted anhydrous mononuclear tris(2,2,6,6-tetramethyl-3,5-heptanedionato) bismuth precursor of the invention may be usefully employed for depositing bismuth or a bismuth-containing film on a substrate, by vaporizing the Lewis base adducted anhydrous mononuclear tris(β-diketonato) bismuth to form a vaporized precursor, and contacting the vaporized precursor with the substrate to deposit bismuth or a bismuth-containing film thereon.

Such deposition may employ liquid delivery and flash vaporization of the Lewis base adducted anhydrous mononuclear tris(β-diketonato) bismuth precursor to form the precursor vapor, and the deposition may be effected by various techniques such as chemical vapor deposition (CVD), including any of various assisted (e.g., plasma-assisted, photoactivated, ion beam-assisted, etc.) CVD methods.

Other aspects, features and embodiments of the invention will be more fully apparent from the ensuing disclosure and appended claims.

DETAILED DESCRIPTION OF THE MENTION, AND PREFERRED EMBODIMENTS THEREOF

Figure 1:
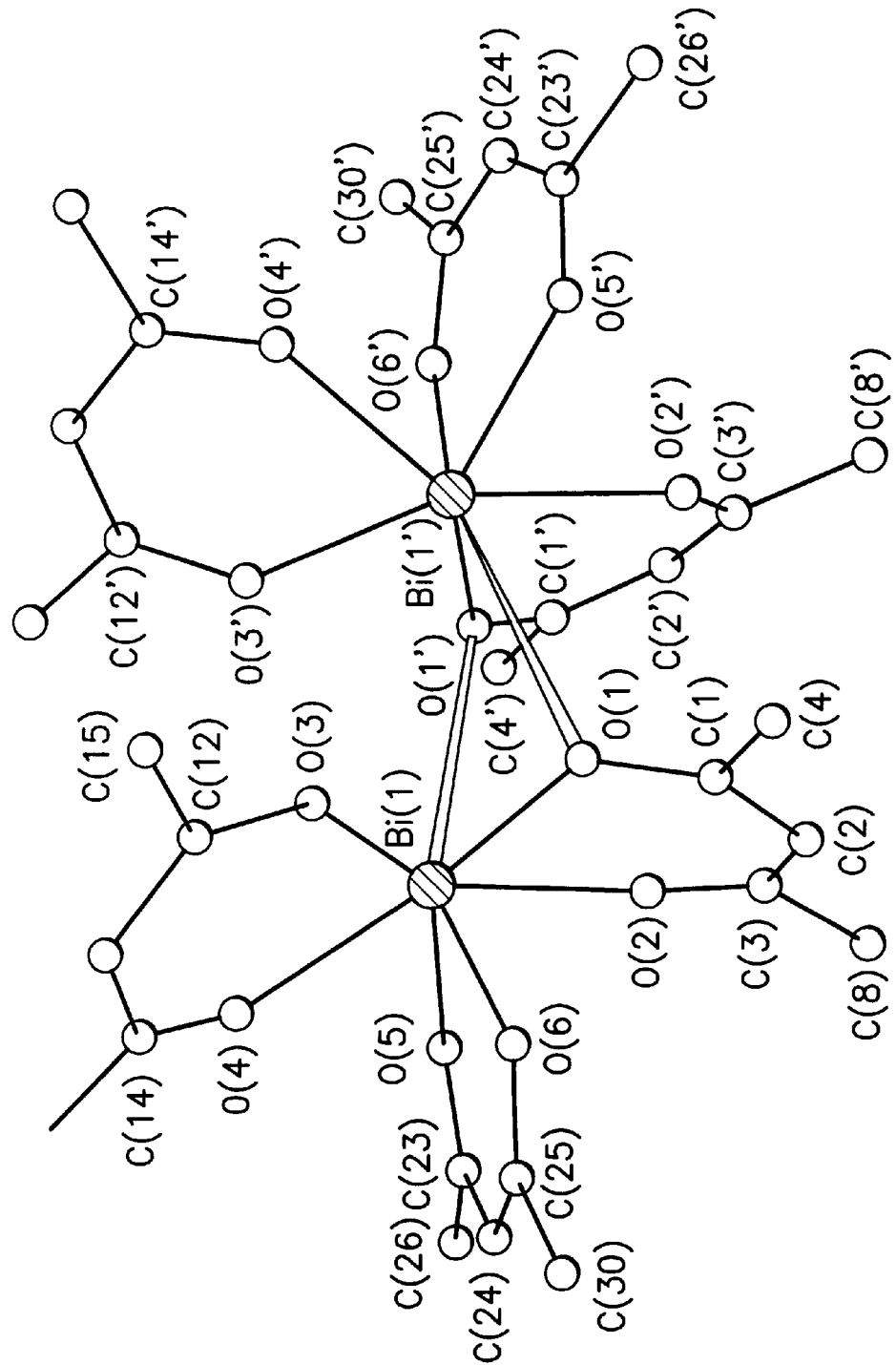
FIGS. 1 and 2 are x-ray crystallographic structural depictions reported in the literature (PRIOR ART) for the dinuclear bismuth complex [Bi(thd)$_3$]2, which is a crystalline white solid with a melting point of 117 ° C.

The present invention relates to the discovery of Lewis base adducts of anhydrous mononuclear forms of tris(β-diketonato) bismuth compositions, e.g., tris(2,2,6,6-tetramethyl-3,5-heptanedionato) bismuth N,N,N'N'-tetramethylethylenediamine, which overcome deficiencies of the prior art dinuclear bismuth complex [Bi(thd)$_3$]2.

As a result of its mononuclear form, the Lewis base adduct bismuth complex of the present invention provides improved thermal transport and more controlled and reproducible gas-phase concentrations than are possible with the prior art dinuclear complexes. These characteristics provide the mononuclear bismuth complexes of the present invention with the ability to form Bi-containing films of superior stoichiometry, morphology and functional performance characteristics, in relation to the films of the prior art formed from the aforementioned dinuclear bismuth complex [Bi(thd)$_3$]2.

As a precursor for the deposition of Bi or Bi-containing films, the previously commercially available dinuclear Bi-thd complex is markedly inferior in respect of its volatility, transport and vaporization properties, being less volatile and more easily decomposed during transport and flash vaporization than desired, and producing higher levels of residue in process equipment upstream of the deposition chamber. The ready susceptibility of the prior art dinuclear bismuth complex [Bi(thd)$_3$]2 to decomposition of the precursor is severely detrimental in a liquid delivery flash vaporization process, where such decomposition leads to premature clogging of the vaporizer as well as undesirable changes in gas-phase concentrations during the deposition process. Such gas-phase concentration variations in turn yield undesirable gradients in deposited film thickness, and in film stoichiometry where the bismuth component is deposited in a multicomponent film.

Unexpectedly, the discovery of the Lewis base adducted mononuclear Bi($\beta$-diketonate)$_3$ complexes of the present invention has provided a solution to such deficiencies of the prior art Bi(thd)$_3$ precursor material. The Lewis base adducted mononuclear Bi($\beta$-diketonate)$_3$ complexes of the present invention are markedly superior to the corresponding dinuclear species, providing improved vaporizer performance, extended vaporizer lifetimes and better control of the Bi-containing film stoichiometry than [Bi(thd)$_3$]$_2$. As a result, the Lewis base adducted Bi($\beta$-diketonate)$_3$ mononuclear complexes of the present invention lead to a more highly reproducible CVD process and improved quality of the deposited film, based on film stoichiometry and uniformity.

While the Lewis base adducted anhydrous mononuclear tris($\beta$-diketonato) bismuth complexes of the present invention are usefully employed in a wide variety of chemical vapor deposition processes for the formation of bismuth-containing films, the complexes have particular utility as a precursor for the vapor-phase deposition of bismuth or bismuth oxide in the formation of ferroelectric thin films and Bi-based superconducting thin film materials. A most preferred use of such Lewis base adducted mononuclear tris($\beta$-diketonato) bismuth complexes is in the formation of ferroelectric Bi-containing thin films for the manufacture of devices such as ferroelectric random access memories. The same materials may be used to deposit bismuth-containing chalcogonides and skutterudites.

The Lewis base adducted mononuclear tris($\beta$-diketonato) bismuth complexes of the invention may be deposited in any suitable manner. For example, the bismuth deposition process may employ liquid delivery and flash vaporization of the Lewis base adducted anhydrous mononuclear tris($\beta$-diketonato) bismuth precursor to form the precursor vapor, and the deposition itself may be effected by chemical vapor deposition (CVD), including any of various assisted (e.g., plasma-assisted) CVD methods, or in any other suitable manner. For purposes of liquid delivery, the Lewis base adducted anhydrous mononuclear tris($\beta$-diketonato) bismuth may be dissolved in any suitable solvent medium, e.g., a single solvent or a multicomponent solvent mixture, compatible with such bismuth reagent.

The disclosure of U.S. patent application Ser. No. 08/975, 372 filed on Nov. 20, 1997 is hereby incorporated herein by reference in its entirety.

A suitable multicomponent solvent mixture for such purpose is a solvent composition comprising solvent species A, B and C, wherein A is a $C_6$–$C_8$ alkane, $C_6$–$C_{10}$ aryl, ether or cyclic ether, B is a $C_8$–$C_{12}$ alkane, and C is a glyme-based solvent (glyme, diglyme, tetraglyme, etc.), polyamine or arylamine in the proportion A:B:C wherein A is from about 2 to about 10 parts by volume, B is from about 0 to about 6 parts by volume, and C is from 0 to about 3 parts by volume. Preferred compositions of A include tetrahydrofuran, toluene and octane and C is often common to the Lewis base adduct of the tris($\beta$-diketonato) bismuth species.

A highly preferred solvent composition of such type comprises octane, decane and a polyamine in approximately 5:4:1 proportion by volume.

Another highly preferred solvent system of such type comprises tetaahydrofiran and a polyamine in approximately 8:2 proportion by volume.

Polyamine species potentially useful as component C in the above-described solvent composition include N,N,N',N'-tetramethylethylenediamine, N,N,N',N',N''-pentamethyldiethylenetriamine, N,N,N',N'', N''',N'''-hexamethyltriethylenetetramine, pyridine or other suitable polyamine component.

The composition of the present invention relates to an anhydrous mononuclear Lewis base adducted bismuth complex, comprising the formula:

wherein A comprises a $\beta$-diketonato ligand and X comprises at least one Lewis base adduct.

More specifically the composition of the present invention relates to an anhydrous mononuclear Lewis base adducted bismuth complex, comprising the formula:

wherein:

A comprises a $\beta$-diketonato ligand having the formula:

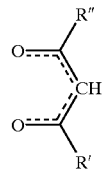

wherein:

R' and R$\Delta$ may be the same or different and are independently selected from H, $C_6$–$C_{10}$ aryl, $C_6$–$C_{10}$ fluoroaryl, $C_6$–$C_{10}$ perfluoroaryl, $C_1$–$C_6$ alkyl, $C_1$–$C_6$ fluoroalkyl, and $C_1$–$C_6$ perfluoroalkyl; and X comprises at least one Lewis base adduct.

More specifically the composition of the present invention relates to an anhydrous mononuclear Lewis base adducted bismuth complex, comprising the formula:

wherein:

A comprises a $\beta$-diketonato ligand selected from the group consisting of:

| | |
|---|---|
| 2,2,6,6-tetramethyl-3,5-heptanedionato | thd |
| 1,1,1-trifluoro-2,4-pentanedionato | tfac |
| 1,1,1,5,5,5-hexafluoro-2,4-pentanedionato | hfac |

-continued

| | |
|---|---|
| 6,6,7,7,8,8,8-heptafluoro-2,2-dimethyl-3,5-octanedionato | fod |
| 2,2,7-trimethyl-3,5-octanedionato | tod |
| 1,1,1,5,5,6,6,7,7,7-decafluoro-2,4-heptanedionato | dfhd |
| 1,1,1-trifluoro-6-methyl-2,4-heptanedionato | tfmhd | and X comprises at least one Lewis base adduct selected from the group consisting of: amines, ethers, glymes, aryls and aryl amines, more specifically, $NH_3$, primary amines, secondary amines, tertiary amines, polyamines, monoglymes, diglymes, triglymes, tetraglymes, polyethers, aliphatic ethers, cyclic ethers, and more specifically, pyridine, toluene, tetrahydrofuran, N,N,N',N'-tetramethylethylenediamine and N,N,N',N',N"-pentamethyldiethylenetriamine.

In one specific method aspect, the present invention relates to a method of synthesis of N,N,N'N'-tetramethylethylenediamine adducted anhydrous mononuclear tris(2,2,6,6-tetramethyl-3,5-heptanedionato) bismuth, by reaction of dinuclear tris(2,2,6,6-tetramethyl-3,5-heptanedionato) bismuth complex and N,N,N',N'-tetramethylethylenediamine in an aprotic solvent under anaerobic conditions.

In another specific method aspect, the present invention relates to a method of synthesis of N,N,N',N',N"-pentamethyldiethylenetriamine adducted anhydrous mononuclear tris(2,2,6,6-tetramethyl-3,5-heptanedionato) bismuth, by reaction of dinuclear tris(2,2,6,6-tetramethyl-3,5-heptanedionato) bismuth complex and N,N,N',N',N"-pentamethyldiethylenetriamine in an aprotic solvent under anaerobic conditions.

In another specific method aspect, the present invention relates to a method of synthesis of N,N,N',N',N"-pentamethyldiethylenetriamine adducted anhydrous mononuclear tris(2,2,6,6-tetramethyl-3,5-heptanedionato) bismuth, by reaction of anhydrous mononuclear tris(2,2,6,6-tetramethyl-3,5-heptanedionato) bismuth and N,N,N',N','N"-pentamethyldiethylenetriamine in an aprotic solvent under anaerobic conditions.

The N,N,N'N'-tetramethylethylenediamine adducted anhydrous mononuclear tris(2,2,6,6-tetramethyl-3,5-heptanedionato) bismuth precursor of the invention may be usefully employed for depositing bismuth or a bismuth-containing film on a substrate, by vaporizing the Lewis base adducted anhydrous mononuclear tris(β-diketonato) bismuth to form a vaporized precursor, and contacting the vaporized precursor with the substrate to deposit bismuth or a bismuth-containing film thereon.

The synthesis of Lewis base adducted anhydrous mononuclear tris(β-diketonato) bismuth complexes of the present invention may be readily carried out in an aprotic solvent medium under anaerobic conditions, and at room temperature and pressure, by reacting at least one molar equivalent of the Lewis base adduct compound with the mononuclear tris(β-diketonato) bismuth of the current art or the dinuclear tris(β-diketonato) bismuth of the prior art in an aprotic solvent medium under anaerobic conditions for sufficient time and at sufficient temperature with subsequent removal of the aprotic solvent medium to yield said anhydrous mononuclear Lewis base adducted tris(β-diketonato) bismuth complex as a reaction product thereof. Purification of the isolated reaction product Lewis base adducted bismuth complex, e.g., by recrystallization, is also advantageously performed in an aprotic medium under anaerobic conditions.

The aprotic solvent may suitably comprise one or more alkanes such as pentane, hexanes, octane, or decane, aryl solvent species such as benzene or toluene, and/or any other suitable aprotic solvent(s) for solution of the mononuclear tris (β-diketonato) bismuth of the current art or the dinuclear tris (β-diketonato) bismuth of the prior art and Lewis base adduct starting materials, wherein such solvents do not preclude the reaction of such starting materials to form the Lewis base adducted mononuclear (β-diketonato) bismuth product.

The foregoing synthesis reaction is carried out under anaerobic conditions, i.e., in the substantial absence, and preferably substantially complete absence, of oxygen. Such anaerobic conditions may for example comprise carrying out the reaction under inert or oxygen-free atmosphere, such as under a nitrogen or argon blanket over the reaction vessel containing the reactants and the aprotic solvent medium. Similarly, the solvents and reactants should be dry and free from water and other protic source constituents.

As an illustrative example of the foregoing synthesis, anhydrous mononuclear tris (2,2,6,6-tetramethyl-3,5-heptanedionato)bismuth N,N,N'N'-tetramethylethylenediamine adduct may be synthesized in accordance with the present invention by reaction of dinuclear tris (2,2,6,6-tetramethyl-3,5-heptanedionato) bismuth complex and N,N,N'N'-tetramethylethylenediamine in hexanes under a nitrogen gas environment.

Figure 2:
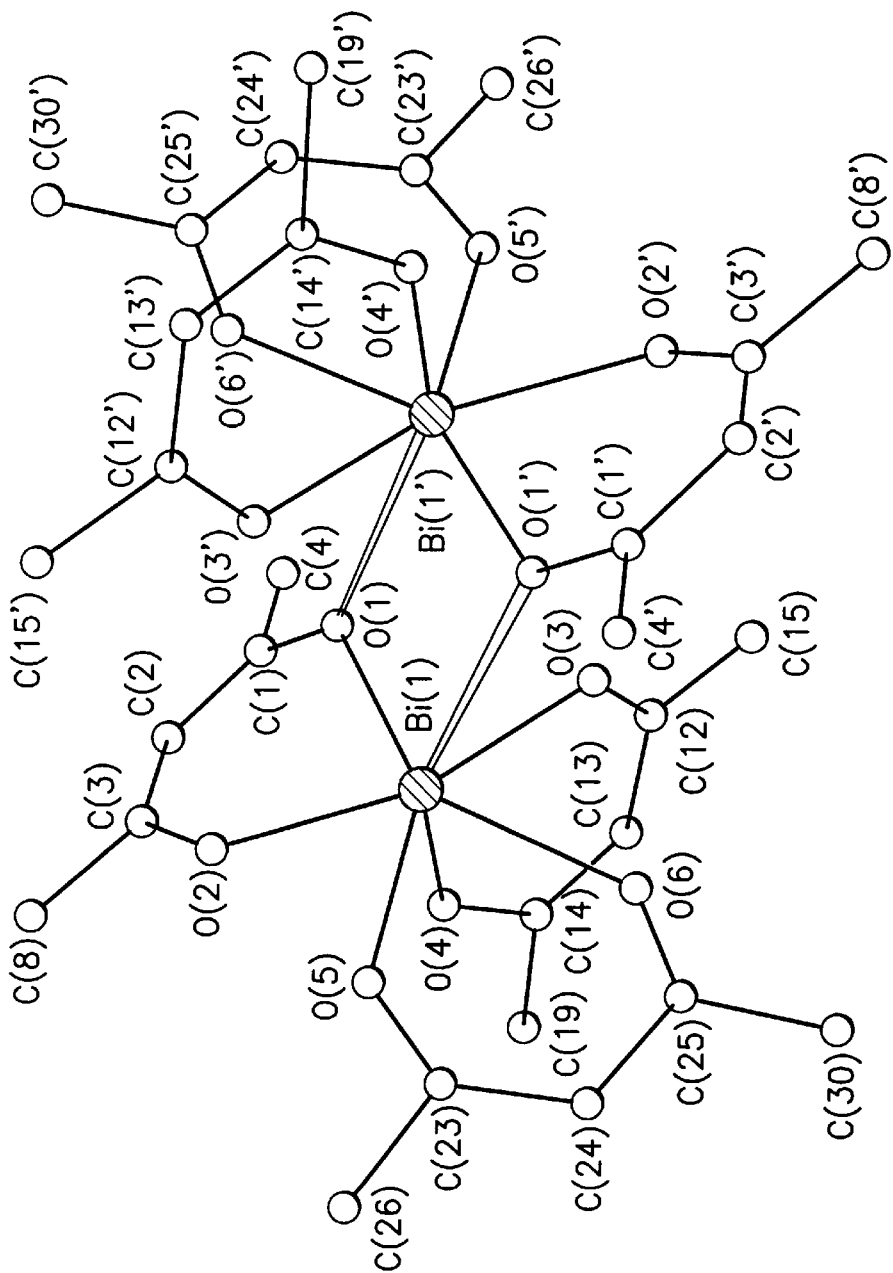

Referring now to the drawings,

FIGS. 1 and 2 are x-ray crystallographic structural depictions reported in the literature for the dinuclear bismuth complex $[Bi(thd)_3]_2$, which is a crystalline white solid with a melting point of 117° C. (Prior Art)

Figure 3:
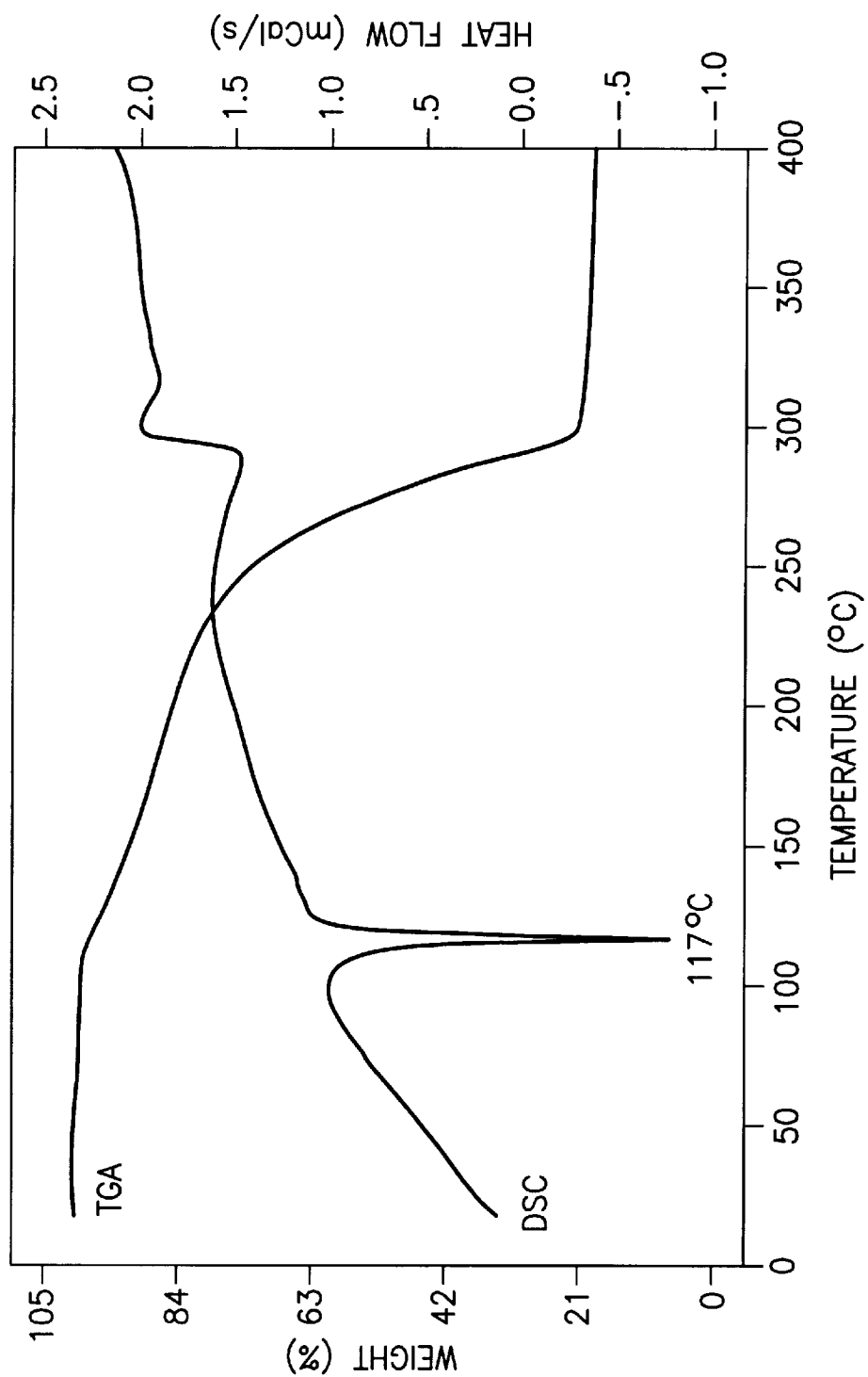
FIG. 3 is a plot of precursor transport (TGA) and melting point (DSC) curves for a representative dinuclear bismuth complex [Bi(thd)$_3$]2 of the prior art.

FIG. 3 is a plot of precursor transport (TGA) and melting point (DSC) curves for a representative dinuclear bismuth complex $[Bi(thd)_3]_2$ of the prior art, having a melting point of 117° C. The literature has variously reported the melting point of such material as being in the range of 112–115° C. This material is inferior in precursor transport properties, as reflected by the TGA plot, showing a gradual weight loss over a wide temperature range during the STA examination.

Figure 4:
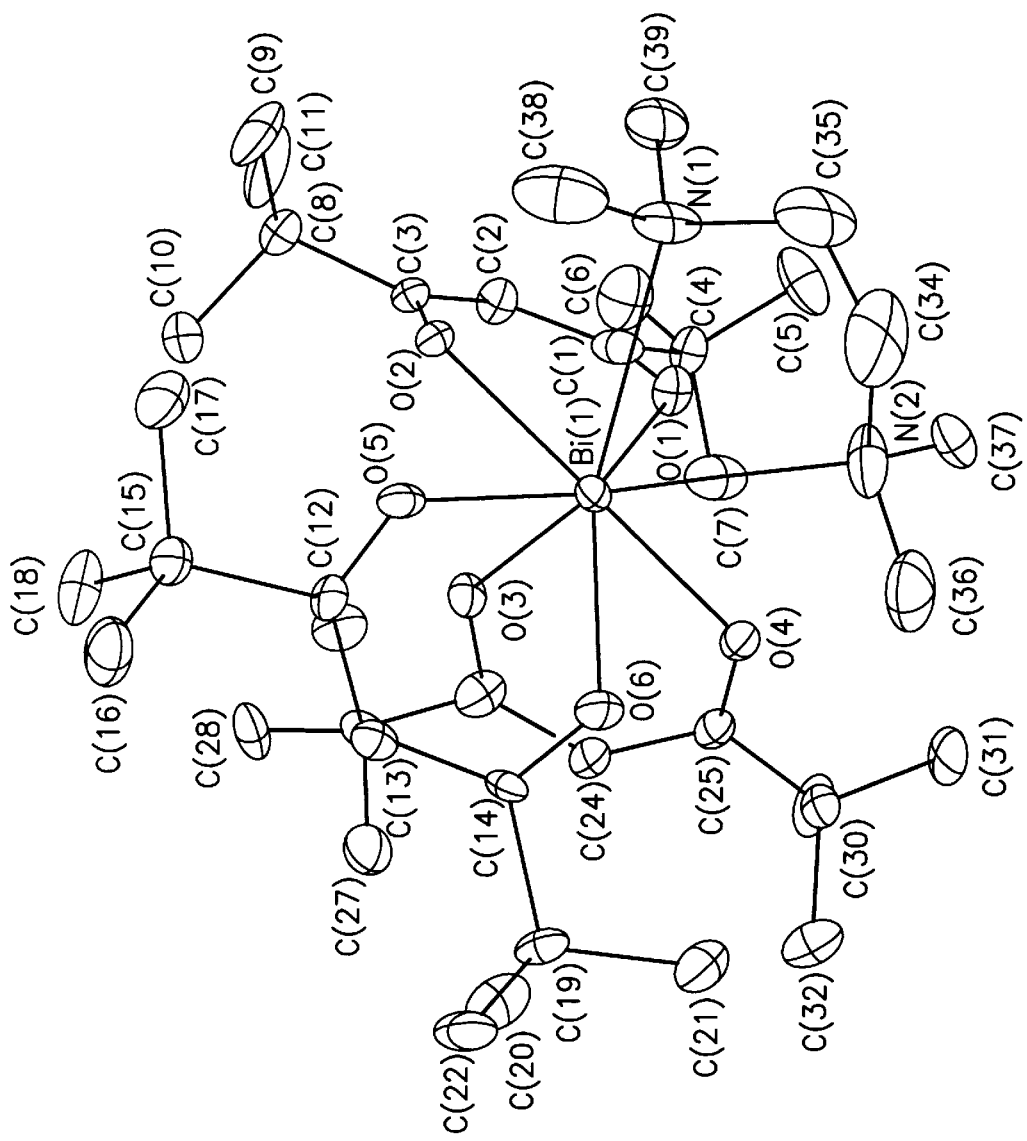
FIG. 4 is a crystal structure determined from a single crystal diffraction analysis of solid N,N,N'N'-tetramethylethylenediamine adducted anhydrous mononuclear tris(2,2,6,6-tetramethyl-3,5-heptanedionato) bismuth of the present invention.

FIG. 4 is a crystal structure determined from a single crystal diffraction analysis of solid N,N,N'N'-tetramethylethylenediamine adducted anhydrous mononuclear tris(2,2,6,6-tetramethyl-3,5-heptanedionato) bismuth of the present invention.

Figure 5:
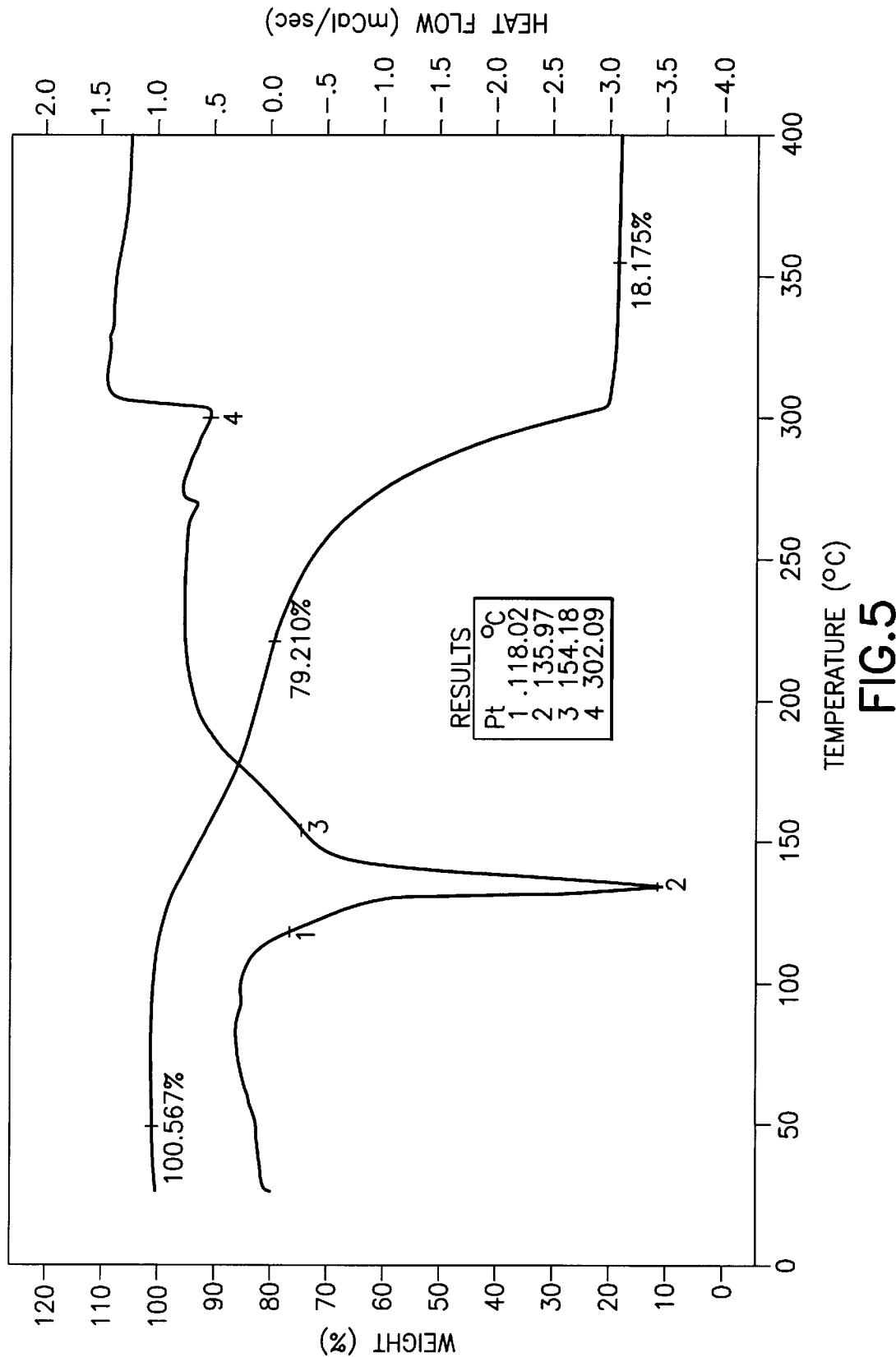
FIG. 5 is a plot of precursor transport (TGA) and melting point (DSC) curves of single crystalline solid, N,N,N'N'-tetramethylethylenediamine adducted anhydrous mononuclear tris(2,2,6,6-tetramethyl-3,5-heptanedionato) bismuth prepared from dinuclear tris(2,2,6,6-tetramethyl-3,5-heptanedionato) bismuth.

FIG. 5 is a plot of precursor transport (TGA) and melting point (DSC) curves of single crystalline solid, N,N,N'N'-tetramethylethylenediamine adducted anhydrous mononuclear tris(2,2,6,6-tetramethyl-3,5-heptanedionato) bismuth prepared from dinuclear tris(2,2,6,6-tetramethyl-3,5-heptanedionato) bismuth. The material exhibits a melting point of about 136° C.

Figure 6:
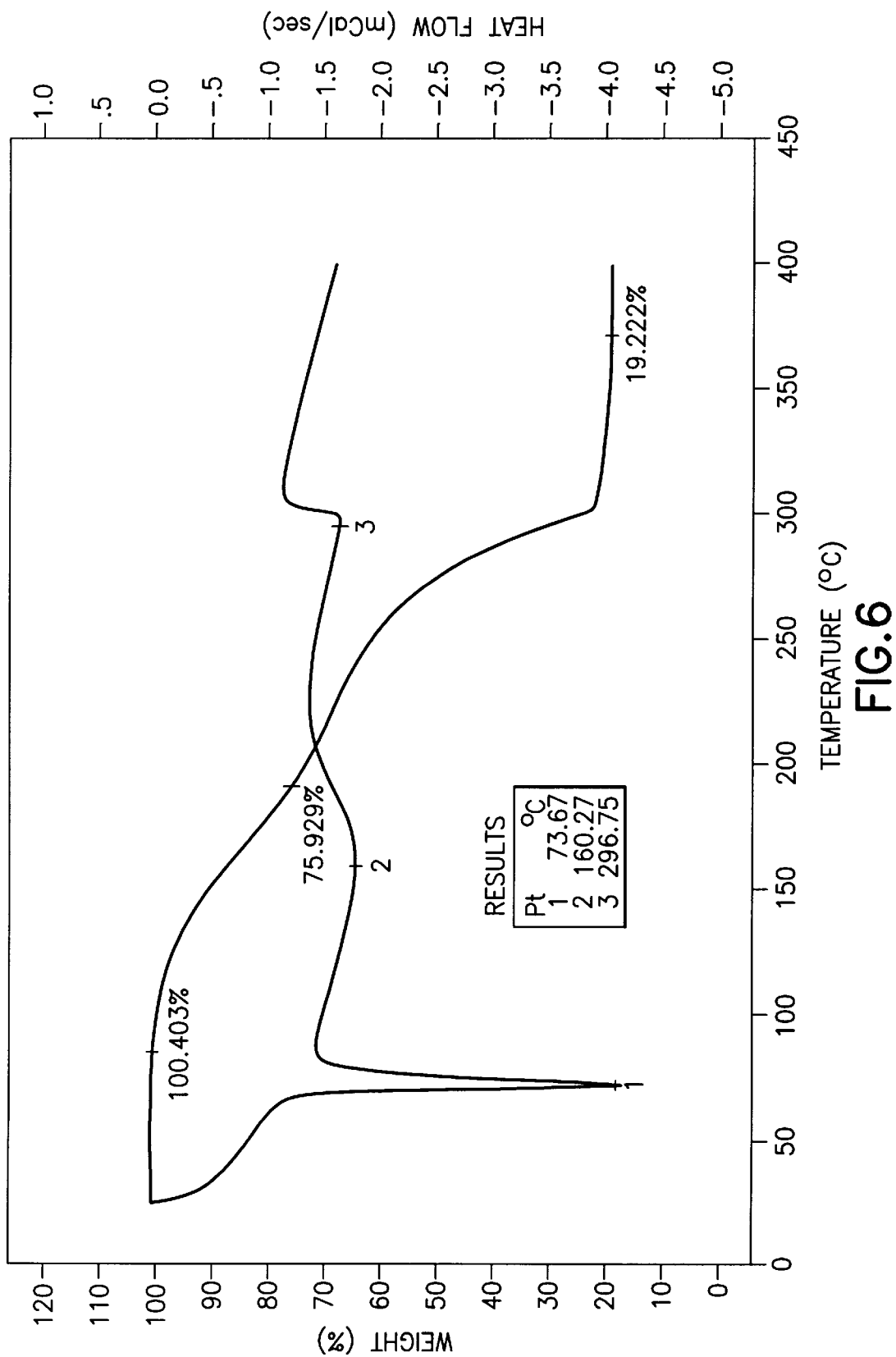
FIG. 6 is a plot of precursor transport (TGA) and melting point (DSC) curves of solid N,N,N',N','N"-pentamethyldiethylenetriamine adducted anhydrous mononuclear tris(2,2,6,6-tetramethyl-3,5-heptanedionato) bismuth prepared from dinuclear tris(2,2,6,6-tetramethyl-3,5-heptanedionato) bismuth.

FIG. 6 is a plot of precursor transport (TGA) and melting point (DSC) curves of solid N,N,N', N','N"-pentamethyldiethylenetriamine adducted anhydrous mononuclear tris(2,2,6,6-tetramethyl-3,5-heptanedionato) bismuth prepared from dinuclear tris(2,2,6,6-tetramethyl-3,5-heptanedionato) bismuth. The material exhibits a melting point of about 73° C.

Figure 7:
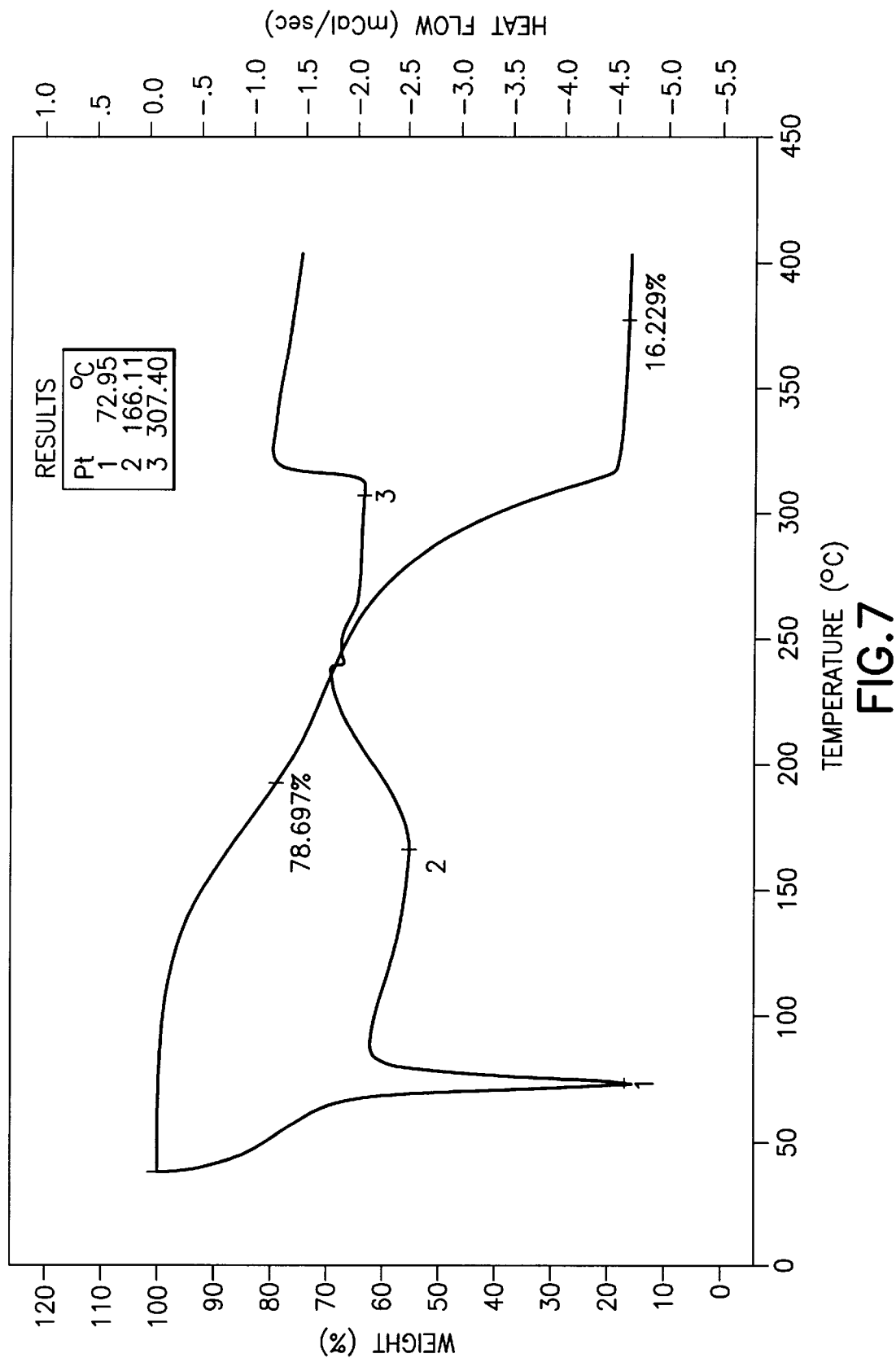
FIG. 7 is a plot of precursor transport (TGA) and melting point (DSC) curves of solid N,N,N',N', 'N"pentamethyldiethylenetriamine adducted anhydrous mononuclear tris(2,2,6,6-tetramethyl-3,5-heptanedionato) bismuth prepared from mononuclear tris(2,2,6,6-tetramethyl-3,5-heptanedionato) bismuth.

FIG. 7 is a plot of precursor transport (TGA) and melting point (DSC) curves of solid N,N,N',N','N"-pentamethyldiethylenetriamine adducted anhydrous mononuclear tris(2,2,6,6-tetramethyl-3,5-heptanedionato) bismuth prepared from mononuclear tris(2,2,6,6-tetramethyl-3,5-heptanedionato) bismuth. The material exhibits a melting point of about 73° C.

Single crystal x-ray diffraction structural determination conclusively shows the Lewis base adducted $Bi(thd)_3$ material of the present invention to be of mononuclear form.

Such material is prepared by addition of the mononuclear tris(β-diketonato) bismuth of the current art or the dinuclear tris(β-diketonato) bismuth of the prior art and Lewis base adduct starting materials, as shown in the plots of FIGS. 6 & 7 wherein both materials exhibit a melting point of about 73° C. The prior art literature reports an x-ray crystal structure which is a dinuclear complex, [Bi(thd)$_3$]$_2$, with excess H(thd) ligand in the crystal lattice.

The Lewis base adducted Bi(thd)$_3$ material of the present invention thus is a mononuclear complex heretofore unknown, and represents a significant advance in the art in the provision of a precursor material having highly attractive characteristics for vaporization, vapor-phase transport, and bismuth deposition, in a wide variety of applications in which bismuth or bismuth-containing films are employed in the fabrication of microelectronic, ferroelectric and superconducting devices or structures.

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art. The invention therefore is to be broadly construed, consistent with the claims hereafter set forth.

What is claimed is:

1. A bismuth Lewis base adduct of the formula:

Bi(A)$_3$·X wherein A is a β-diketonato ligand and X is a Lewis base ligand selected from the group consisting of: amines, ethers, glymes, aryls and aryl amines.

2. The bismuth Lewis base adduct according to claim 1, wherein the β-diketonato ligand comprises the formula:

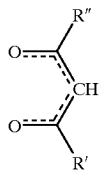

wherein R' and R" may be same or different and are independently selected from the group consisting of H, C$_6$–C$_{10}$ aryl, C$_6$–C$_{10}$ fluoroaryl, C$_6$–C$_{10}$ perfluoroaryl, C$_1$–C$_6$ alkyl, C$_1$–C$_6$ fluoroalkyl and C$_1$–C$_6$ perfluoroalkyl.

3. The bismuth Lewis base adduct according to claim 1, wherein the β-diketonato ligand is selected from the group consisting of:
   2,6,6-tetramethyl-3,5-heptanedionato;
   1,1,1-trifluoro-2,4-pentanedionato;
   1,1,1,5,5,5-hexafluoro-2,4-pentanedionato;
   6,6,7,7,8,8,8-heptafluoro-2,2-dimethyl-3,5-octanedionato;
   2,2,7-trimethyl-3,5-octanedionato;
   1,1,1,5,5,6,6,7,7,7-decafluoro-2,4-heptanedionato; and
   1,1,1-trifluoro-6-methyl-2,4-heptanedionato.

4. The bismuth Lewis base adduct according to claim 1, wherein the Lewis base ligand is selected from the group consisting of: NH3, primary amines, secondary amines, tertiary amines and polyamines.

5. The bismuth Lewis base adduct according to claim 1, wherein the Lewis base ligand is selected from the group consisting of: monoglymes, diglymes, triglymes, tetraglymes, aliphatic ethers, polyethers, and cyclic ethers.

6. The bismuth Lewis base adduct according to claim 1, wherein the Lewis base ligand is tetrahydrofuran.

7. The bismuth Lewis base adduct according to claim 1, wherein the Lewis base ligand is selected from the group consisting of toluene and pyridine.

8. The bismuth Lewis base adduct according to claim 1, wherein the Lewis base ligand is selected from the group consisting of: N,N,N',N'-tetramethylethylenediamine and N,N,N',N',N"-pentamethyldiethylenetriamine.

9. A Lewis base adduct of tris(2,2,6,6-tetramethyl-3,5-heptanedionato) bismuth, wherein the Lewis base is selected from the group consisting of: amines, ethers, glymes, aryls and aryl amines.

10. A N,N,N'N'-tetramethylethylenediamine adduct of anhydrous mononuclear tris(2,2,6,6-tetramethyl-3,5-heptanedionato) bismuth having a melting point of about 136° C.

11. A N,N,N'N'-tetramethylethylenediamine adduct of anhydrous mononuclear tris(2,2,6,6-tetramethyl-3,5-heptanedionato) bismuth having the x-ray crystallographic structure shown in FIG. 4.

12. A method of synthesizing an adduct of anhydrous mononuclear tris(β-diketonato) bismuth, comprising reacting at least one molar equivalent of a Lewis base ligand selected from the group consisting of: amines, ethers, glymes, aryls and aryl amines, with a tris (β-diketonato) bismuth compound in an aprotic solvent medium under anaerobic conditions at sufficient temperature for sufficient time with subsequent removal of the aprotic solvent medium to yield said adduct of anhydrous mononuclear tris(β-diketonato) bismuth as a reaction product thereof.

13. The method according to claim 12, wherein the aprotic solvent medium comprises a solvent selected from the group consisting of aryls, ethers and aryl amines.

14. The method according to claim 12, wherein the aprotic solvent medium comprises a solvent selected from the group consisting of pentane, hexane, octane, decane, tetrahydrofuran, benzene, toluene and pyridine.

15. The method according to claim 12, wherein the tris (β-diketonato) bismuth compound is mononuclear and the β-diketonato is selected from the group consisting of:
   2,2,6,6-tetramethyl-3,5-heptanedionato;
   1,1,1-trifluoro-2,4-pentanedionato;
   1,1,1,5,5,5-hexafluoro-2,4-pentanedionato;
   6,6,7,7,8,8,8-heptafluoro-2,2-dimethyl-3,5-octanedionato;
   2,2,7-trimethyl-3,5-octanedionato;
   1,1,1,5,5,6,6,7,7,7-decafluoro-2,4-heptanedionato; and
   1,1,1-trifluoro-6-methyl-2,4-heptanedionato.

16. The method according to claim 12, wherein the tris (β-diketonato) bismuth compound is dinuclear and the β-diketonato is selected from the group consisting of:
   2,2,6,6-tetramethyl-3,5-heptanedionato;
   1,1,1-trifluoro-2,4-pentanedionato;
   1,1,1,5,5,5-hexafluoro-2,4-pentanedionato;
   6,6,7,7,8,8,8-heptafluoro-2,2-dimethyl-3,5-octanedionato;
   2,2,7-trimethyl-3,5-octanedionato;
   1,1,1,5,5,6,6,7,7,7-decafluoro-2,4-heptanedionato; and
   1,1,1-trifluoro-6-methyl-2,4-heptanedionato.

17. The method according to claim 12, wherein the Lewis base ligand is selected from the group consisting of: NH$_3$, primary amines, secondary amines, tertiary amines and polyamines.

18. The method according to claim 12, wherein the Lewis base ligand is selected from the group consisting of:

monoglymes, diglymes, triglymes, tetraglymes, aliphatic ethers, polyethers, and cyclic ethers.

19. The method according to claim 12, wherein the Lewis base ligand is tetrahydrofuran.

20. The method according to claim 12, wherein the Lewis base ligand is toluene.

21. The method according to claim 12, wherein the Lewis base ligand is selected from the group consisting of: N,N,N',N'-tetramethylethylenediamine and N,N,N',N',N''-pentamethyldiethylenetriamine.

22. A method of synthesizing a Lewis base adduct of anhydrous mononuclear tris(2,2,6,6-tetramethyl-3,5-heptanedionato) bismuth, comprising: reacting anhydrous mononuclear tris(2,2,6,6-tetramethyl-3,5-heptanedionato) bismuth and N,N,N'N'-tetramethylethylenediamine in hexanes under a nitrogen gas environment.

23. A method of synthesizing a Lewis base adduct of anhydrous mononuclear tris(2,2,6,6-tetramethyl-3,5-heptanedionato) bismuth, comprising: reacting dinuclear tris(2,2,6,6-tetramethyl-3,5-heptanedionato) bismuth and N,N,N'N'-tetramethylethylenediamine in hexanes under a nitrogen gas environment.

24. A Lewis base adduct of anhydrous mononuclear bismuth comprising a β-diketonato ligand and at least one Lewis base ligand, wherein the Lewis base ligand is selected from the group consisting of: amines, ethers, glymes, aryls and aryl amines.

* * * * *